(12) United States Patent
Maschio et al.

(10) Patent No.: US 11,717,439 B2
(45) Date of Patent: Aug. 8, 2023

(54) ROTATIONAL CUTTER

(71) Applicant: Alcon Inc., Fribourg (CH)

(72) Inventors: Niccolo Maschio, Winterthur (CH); Niels Alexander Abt, Winterthur (CH); Reto Grueebler, Greifensee (CH); Philipp Schaller, Stein am Rhein (CH); Timo Jung, Winterthur (CH); Rodolfo Wolfer, Schaffhausen (CH)

(73) Assignee: Alcon Inc., Fribourg (CH)

( * ) Notice: Subject to any disclaimer, the term of this patent is extended or adjusted under 35 U.S.C. 154(b) by 268 days.

(21) Appl. No.: 16/884,335

(22) Filed: May 27, 2020

(65) Prior Publication Data

US 2020/0375797 A1 Dec. 3, 2020

Related U.S. Application Data

(60) Provisional application No. 62/854,582, filed on May 30, 2019.

(51) Int. Cl.
*A61F 9/007* (2006.01)

(52) U.S. Cl.
CPC .............. *A61F 9/00763* (2013.01)

(58) Field of Classification Search
CPC ....... B26B 19/12; B26B 19/284; B26B 19/02; A61F 9/00763; A61F 9/007; A61F 9/00745; A61F 9/00736; A61B 17/3207; A61B 17/320758; A61B 2017/320004; A61B 17/32002
See application file for complete search history.

(56) References Cited

U.S. PATENT DOCUMENTS

| | | |
|---|---|---|
| 2,177,791 A * | 10/1939 | Smith .................... B26B 19/02 30/43.2 |
| 3,008,233 A | 11/1961 | Waggoner |
| 4,118,863 A | 10/1978 | Sandy |
| 5,230,153 A | 7/1993 | Andis |
| 6,317,982 B1 | 11/2001 | Andrew |
| 8,298,253 B2 | 10/2012 | Charles |
| 10,555,834 B2 | 2/2020 | Charles |
| 10,675,180 B2 | 6/2020 | Grueebler |
| 10,729,582 B2 | 8/2020 | Biancalana |
| 2017/0360603 A1* | 12/2017 | Grueebler ........... A61F 9/00709 |
| 2018/0085943 A1 | 3/2018 | Bady et al. |
| 2018/0271705 A1 | 9/2018 | Valencia |

OTHER PUBLICATIONS

Alcon Global Vitreoretinal Product Catalog, V2, Feb. 2014, pp. 29-47.

* cited by examiner

*Primary Examiner* — Ashley L Fishback
*Assistant Examiner* — Chima U Igboko
(74) *Attorney, Agent, or Firm* — Patterson + Sheridan, LLP

(57) ABSTRACT

Particular embodiments disclosed herein provide a rotational cutter for delaminating a membrane from a retina of an eye. The rotational cutter may comprise a first shaft and a second shaft comprising a blade portion, wherein the second shaft is coupled to a driver that is configured to at least partially rotate the second shaft relative to the first shaft, wherein rotating the second shaft rotates the blade portion for delaminating the membrane. The rotational cutter may also comprise a bottom portion configured to interface with a surface of the retina, wherein the bottom portion comprises one or more curved edges.

5 Claims, 6 Drawing Sheets

ROTATIONAL CUTTER

PRIORITY CLAIM

This application claims the benefit of priority of U.S. Provisional Patent Application Ser. No. 62/854,582 titled "Rotational Cutter", filed on May 30, 2019, whose inventors are Niccolo Maschio, Niels Alexander Abt, Reto Grueebler, Philipp Schaller, Timo Jung, and Rodolfo Wolfer, which is hereby incorporated by reference in its entirety as though fully and completely set forth herein.

TECHNICAL FIELD

The present disclosure relates generally to a rotational cutter for ophthalmic surgery.

BACKGROUND

Membrane removal is a useful surgical treatment for different macular surface diseases. A membrane generally refers to a very thin layer of scar tissue that forms on the surface of the retina. Different types of membranes include internal limiting membranes (ILM), epi-retinal membranes (ERM), and proliferative membranes. Each of these membranes may develop as a result of a different eye disease or condition. For example, in the case of ERMs, the scar tissue formation can be associated with a number of ocular conditions, such as prior retinal tears or detachments, or retinal vascular diseases, such as diabetic retinopathy or venous occlusive disease. ERMs can also be developed due to trauma associated with ocular surgery or be associated with intraocular (inside the eye) inflammation. In another example, proliferative membranes may be caused by diabetic retinopathy, which in its advanced form causes new abnormal blood vessels to proliferate (increase in number) on the surface of the retina, thereby forming a proliferative membrane.

Surgical techniques for the removal or peeling of membranes require skill and patience. Precise and carefully constructed surgical instruments are used for each segment of the surgical technique. The surgical treatment itself includes grasping an edge of the membrane, and peeling the membrane. However, peeling certain membranes may pose additional complexities because the membranes may have developed tissues or vessels (referred to herein as "connective tissues") that attach the membranes to the retina. Accordingly, in such cases, the surgeon has to delaminate or remove the connective tissues between the membrane and the retina in order to continue to peel the membrane. Currently, a surgeon may use scissors to delaminate the connective tissue. However, scissors may damage the surface of the retina.

BRIEF SUMMARY

The present disclosure relates generally to a rotational cutter for ophthalmic surgery.

Particular embodiments disclosed herein provide a rotational cutter for delaminating a membrane from a retina of an eye. The rotational cutter may comprise a first shaft and a second shaft comprising a blade portion, wherein the second shaft is coupled to a driver that is configured to at least partially rotate the second shaft relative to the first shaft, wherein rotating the second shaft rotates the blade portion for delaminating the membrane. The rotational cutter may also comprise a bottom portion configured to interface with a surface of the retina, wherein the bottom portion comprises one or more curved edges.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide a rotational cutter for ophthalmic surgery.

Figure 1B:
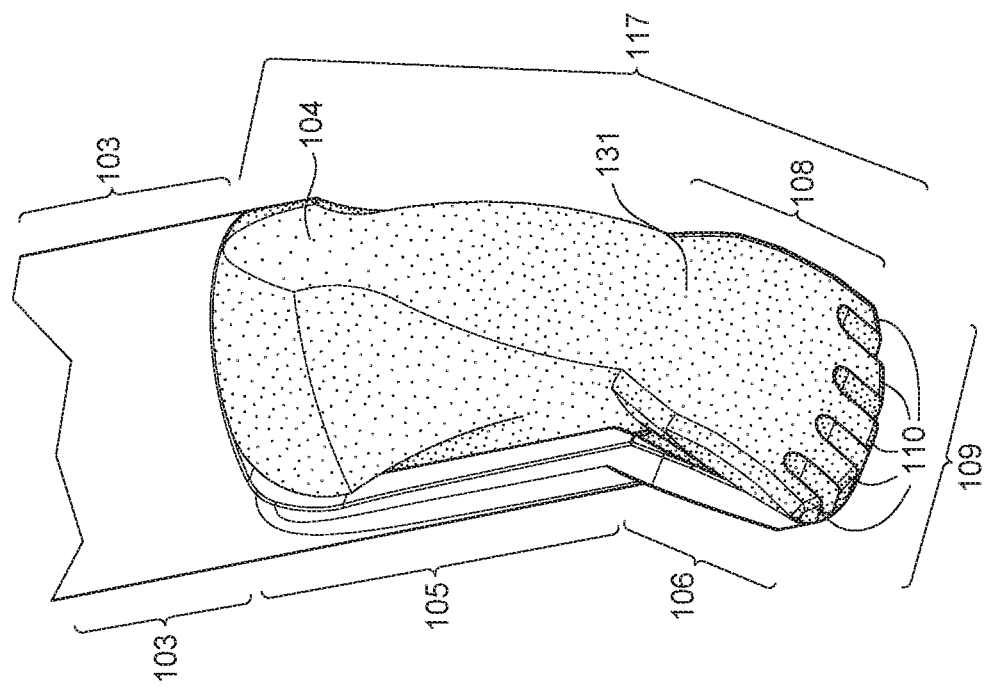
FIG. 1B illustrates a back view of the rotational cutter of FIG. 1A, in accordance with certain embodiments of the present disclosure.
Figure 1A:
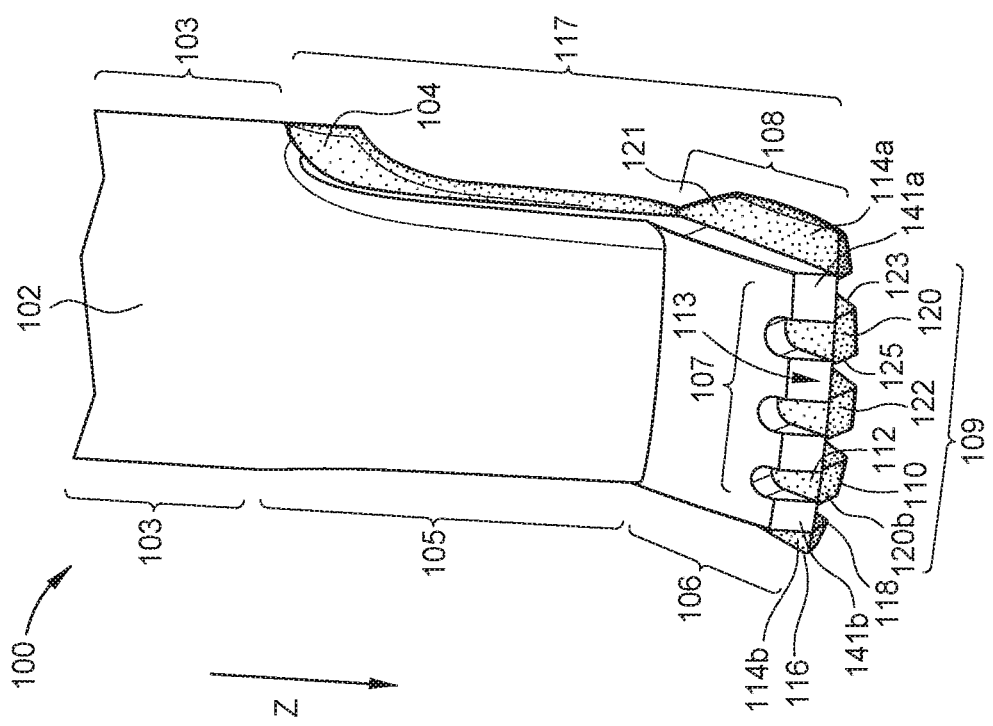
FIG. 1A illustrates an example rotational cutter, in accordance with certain embodiments of the present disclosure.

FIG. 1A illustrates an example rotational cutter 100, in accordance with certain embodiments of the present disclosure. Rotational cutter 100 includes an outer shaft 102 and an inner shaft 104. Outer shaft 102 comprises a cylindrical portion 103 at its proximal end, a blade portion 106 at its distal end, and an extension 105 that connects the cylindrical portion 103 and the blade portion 106. Upper blade portion 106 includes a plurality of upper teeth 107, each of which includes a sharp and acute tip 113 for cutting connective tissue. In the example of FIG. 1A, upper teeth 107 include four teeth, wherein three gaps separate the four teeth from each other. Upper teeth 107 include two outer teeth 141a, 141b and two inner teeth (not separately labeled).

Cylindrical portion 103 of outer shaft 102 is disposed around and houses at least a portion of inner shaft 104. Inner shaft 104 comprises a proximal portion that is housed by cylindrical portion 103 and a distal portion 117 that extends beyond cylindrical portion 103. Distal portion 117 includes a lower blade portion 108 that abuts against the upper blade portion 106 of outer shaft 102. Specifically, lower blade portion 108 includes an inner surface 121 that interfaces with the inner surface (not shown) of upper blade portion 106.

Lower blade portion 108 comprises a plurality of lower teeth 109. In the example of FIG. 1A, lower teeth 109 include two outer teeth 114a, 114b, two inner teeth 120a, 120b, and one middle tooth 122. These five lower teeth are separated by four gaps. In addition, as shown in FIG. 1A, lower teeth 109 may have different geometries, such as different heights or thicknesses, as compared to each other. For example, each of outer teeth 114a, 114b includes an outer side 116 and an inner side 118. An outer tooth 114 has a smaller height at its outer side 116 than its inner side 118. Similarly, each of inner teeth 120a, 120b also has an outer side 123 and an inner side 125. An inner tooth 120 has a smaller height at its outer side 123 than its inner side 125. Middle tooth 122 may have the same height on each of its sides. Additionally, each of lower teeth 109 includes a rounded or curved bottom edge 110 and a sharp upper edge or tip 112. These rounded bottom edges 110 reduce the risk of any potential damage that placing rotational cutter 100 on the surface of the retina may cause to the retina, while the sharp upper edges 112 are used for cutting connective tissues. Together, the rounded bottom edges 110 and different tooth heights give the lower teeth 109, collectively, a generally rounded, or arcuate, bottom profile configured to interface the retina.

Outer shaft 102 is configured to oscillate (or partially rotate) with respect to inner shaft 104 and around a longitudinal axis of inner shaft 104 (e.g., axis Z, which is also parallel to the longitudinal axis of outer shaft 102) when rotational cutter 100 is in operation. In one example, outer shaft 102 is coupled to a driver such as an electromechanical motor (e.g., stepper motor) that oscillates outer shaft 102 around and with respect to inner shaft 104. In another example, outer shaft 102 may be coupled to a driver such as a handle, which may be a hand activated handle (e.g., RENAISSANCE® Handle sold by Alcon Vision, LLC of Fort Worth, Tex.) or an automated handle (e.g., CONSTELLATION® Vision System Pneumatic Handpiece sold by Alcon Vision, LLC of Fort Worth, Tex.) that is connected to a console. In such an example, the handle may work to create longitudinal or linear motion that may then be converted to rotary or rotational motion by a mechanism to rotate outer shaft 102. The mechanism may be part of the handle or may be a separate from the handle. In some embodiments, the mechanism may be referred to as a rotational spin-split mechanism.

Figure 2B:
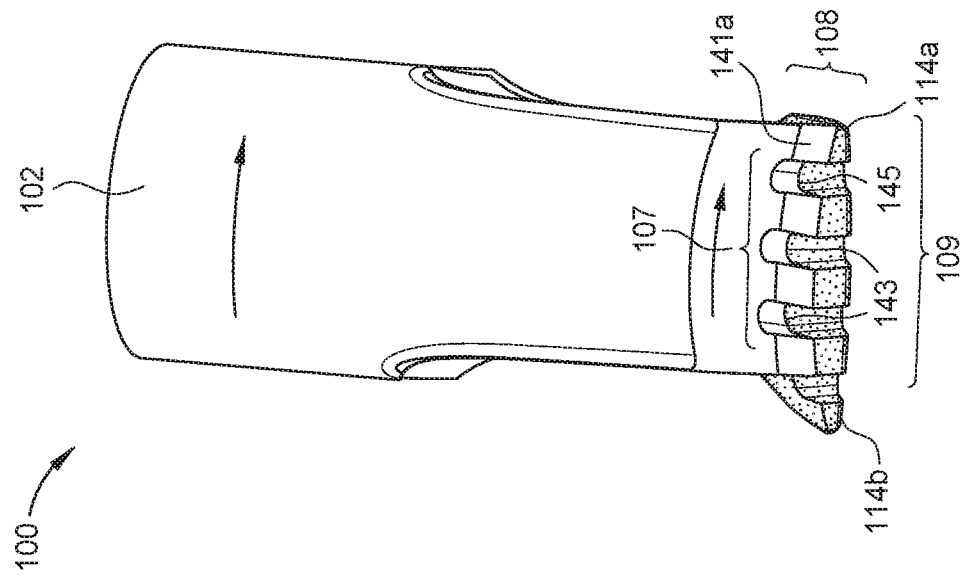
FIGS. 2A-2B illustrate an example oscillating motion of an outer shaft of the rotational cutter of FIGS. 1A-1B with respect to an inner shaft of the rotational cutter, in accordance with certain embodiments of the present disclosure.
Figure 2A:
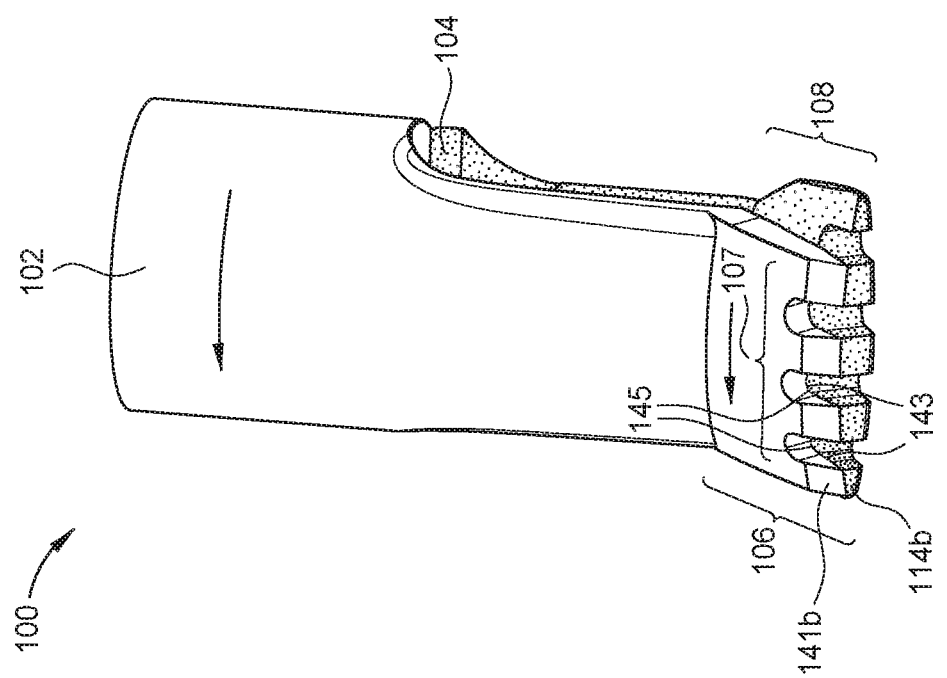

The oscillation of outer shaft 102 around inner shaft 104 causes upper teeth 107 to slide sideways with respect to lower teeth 109, as further illustrated in relation to FIGS. 2A-2B. The oscillating and sideways motion of upper teeth 107 with respect to lower teeth 109 enables rotational cutter 100 to cut connective tissues between a membrane and the surface of the retina without damaging the retina.

FIG. 1B illustrates a back view of rotational cutter 100. As shown, the back of exposed segment 117 of inner shaft 104 has a curved surface. This is to ensure that the back of exposed segment 117 does not cause damage to the surface of the retina when rotational cutter 100 is placed thereon. The back of exposed segment 117 includes the back of blade portion 108, which is also referred to as the outer surface 131 of lower blade portion 108. FIG. 1B also shows rounded bottom edges 110 of lower teeth 109, which reduce the risk of damage to the surface of the retina when lower teeth 109 are placed in contact with the retina. Outer surface 131 of lower blade portion 108 is also referred to as a bottom portion of rotational cutter 100. The bottom portion of rotational cutter 100 is configured to interface or make contact with the surface of the retina.

FIGS. 2A-2B illustrate the oscillating motion of outer shaft 102 with respect to inner shaft 104. For example, FIG. 2A illustrates outer shaft 102 after it has been rotated in a first direction (e.g., left) and about a longitudinal axis of inner shaft 104. As shown, outer shaft 102's rotation in the first direction causes upper blade portion 106 to slide sideways to the first direction with respect to lower blade portion 108. The rotation of outer shaft 102 in the first direction may end when the gaps in-between upper teeth 107 are aligned with at least some of the gaps in-between lower teeth 109 and/or when outer tooth 141b and outer tooth 114b are aligned (e.g., when the outer sides of outer tooth 141b and outer tooth 114b are flush with each other).

FIG. 2B illustrates outer shaft 102 after it has been rotated in a second direction (e.g., right) and about a longitudinal axis of inner shaft 104. Outer shaft 102's rotation in the second direction causes upper blade portion 106 to also slide sideways in the second direction with respect to lower blade portion 108. Outer shaft 102's rotation in the second direction may end when the gaps in-between upper teeth 107 are aligned with at least some of the gaps in-between lower teeth 109 and/or when outer tooth 141a and outer tooth 114a are aligned. The oscillating motion of outer shaft 102 causes upper blade portion 106 to move back and forth between the position shown in FIG. 2A and the position shown in FIG. 2B with a certain frequency.

FIGS. 2A and 2B also illustrate the sharp side edges 143 of lower teeth 109 and the sharp side edges 145 of upper teeth 107. More specifically, each one of upper teeth 107 includes sharp side edges, such as sharp side edge 145, on both sides, except for outer teeth 14l a-b, which have sharp side edges only on their inner sides. Similarly, each one of lower teeth 109 includes sharp side edges, such as sharp side edge 143, on both sides, except for outer teeth 114a-b, which have sharp side edges only on their inner sides. When rotational cutter 100 is operational (i.e., when outer shaft 102 oscillates as described above), tissue (e.g., connective tissue connecting an ILM or ERM to the retina) may get caught in-between the gaps of upper teeth 107 and lower teeth 109 and then get severed, or cut, as upper teeth 107 move from side to side. For example, tissue may be severed when it is caught in between a sharp side edge 145 of one of the upper teeth 107 and a sharp side edge 143 of one of the lower teeth 109. The sharp tips 113 of upper teeth 107 and the sharp tips 112 of the lower teeth 109 also work to cut any connective tissue that may come in contact with them.

In certain embodiments, a surgeon may insert rotational cutter 100 into a patient's eye through an insertion cannula. An insertion cannula may be inserted into the eye after making a small incision in the sclera and pars plana. The insertion cannula is configured to allow the user to insert various surgical devices into the eye without causing trauma to the surrounding tissue (e.g., sclera, pars plana). Accordingly, configuring outer shaft 102 to rotate around and with respect to inner shaft 104 in an oscillatory manner is advantageous because of the limited amount of space available inside an insertion cannula through which rotational cutter 100 may be inserted into the eye during the operation. In other words, the configuration of rotational cutter 100 allows for operation of rotational cutter 100 and its components while inserted through the limited space that is available inside an insertion cannula.

Figure 3:
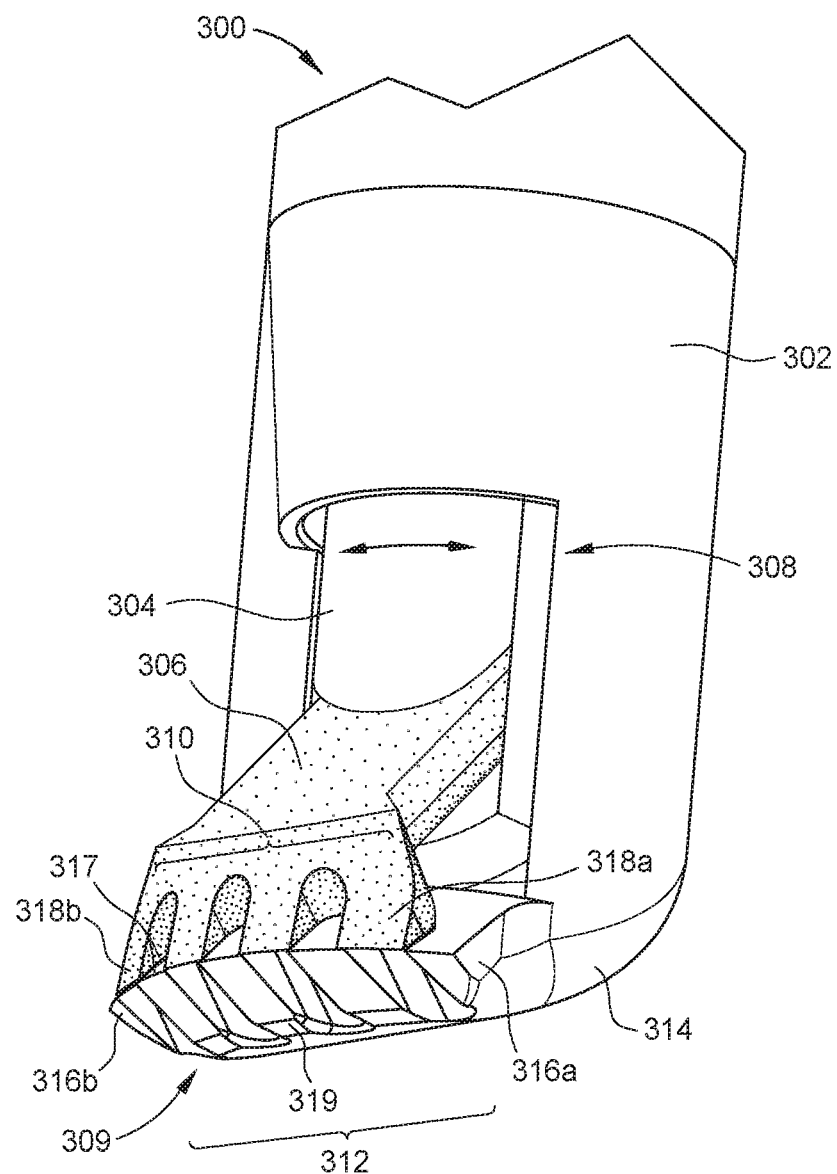
FIG. 3 illustrates another example rotational cutter, in accordance with certain embodiments of the present disclosure.

FIG. 3 illustrates another rotational cutter 300 including an outer shaft 302 and an inner shaft 304. Unlike rotational cutter 100 (shown in FIGS. 1A-2B), in which a portion of inner shaft 104 was configured to interface with the surface of the retina, in rotational cutter 300, a portion of outer shaft 302 is configured to interface with the surface of the retina. Specifically, outer shaft 302 includes a curved bottom portion 314 on its distal end that is configured to be placed on the surface of the retina. (Bottom portion 314 may also be referred to as the bottom portion of rotational cutter 300.) Because bottom portion 314 is curved and has curved or rounded edges, placing rotational cutter 300 on the surface of the retina does not cause damage to the retina. On its distal end, outer shaft 302 also comprises a lower blade portion 309 including a plurality of lower teeth 312 with gaps in between the individual teeth. Each one of lower teeth 312 has a sharp tip 317 for cutting connective tissue that may come in contact with them. Also, each one of lower teeth 312 includes a sharp side edge on each of its side, except for outer teeth 316a and 316b, which have sharp side edges only on their inner sides. Lower teeth 312 also have curved bottoms 319, which merge into bottom portion 314, and which reduce the risk of any potential damage that placing rotational cutter 300 on the surface of the retina may cause to the retina.

Outer shaft 302 is disposed around and houses at least a portion of inner shaft 304, which is configured to rotate within and with respect to outer shaft 302. Accordingly, inner shaft 304 has an outer diameter that is smaller than the inner diameter of outer shaft 302. Inner shaft 304 includes an upper blade portion 306 that extends, at an angle, out of an opening 308 near the distal end of outer shaft 302. Upper blade portion 306 includes a plurality of upper teeth 310 with gaps in between the individual teeth. Upper teeth 310 interface with the upper surfaces of lower teeth 312. Each upper tooth 310 has a sharp tip 311 that is used for cutting connective tissue. Upper teeth 310 are also configured to slide sideways with respect to lower teeth 312 as a result of the rotational and oscillating movement of inner shaft 304 with respect to outer shaft 302. More specifically, inner shaft 304 rotates in an oscillating manner in a first direction (e.g., left) and a second direction (e.g., right). In certain embodiments, inner shaft 304 is coupled to a driver (e.g., motor or a handle, as described above) that rotates inner shaft 304 in an oscillating manner with a certain frequency.

The rotation of inner shaft 304 in the first direction causes upper blade portion 306 to slide sideways to the first direction with respect to lower blade portion 309. The rotation of inner shaft 304 in the first direction (e.g., left) may end when gaps in-between upper teeth 310 are aligned with at least some of the gaps in-between lower teeth 312 and/or when outer tooth 318a of upper teeth 310 and outer tooth 316a of lower teeth 312 are aligned (e.g., when the outer sides of outer tooth 318a and outer tooth 316a are flush with each other). The rotation of inner shaft 304 in the second direction (e.g., right) may end when gaps in-between upper teeth 310 are aligned with at least some of the gaps in-between lower teeth 312 and/or when outer tooth 318b of upper teeth 310 and outer tooth 316b of lower teeth 312 are aligned.

Similar to rotational cutter 100, when rotational cutter 300 is operational (i.e., when inner shaft 304 oscillates as described above), connective tissue may get caught in the gaps between upper teeth 310 and lower teeth 312 and get severed or cut as upper teeth 310 move from side to side. For example, a connective tissue may be severed when it is caught in between a sharp side edge of one of the upper teeth 310 and a sharp side edge of one of the lower teeth 312. The sharp tips 311 of upper teeth 312 and sharp tips 317 of lower teeth 312 also work to cut any connective tissue that may come in contact with them.

Figure 4A:
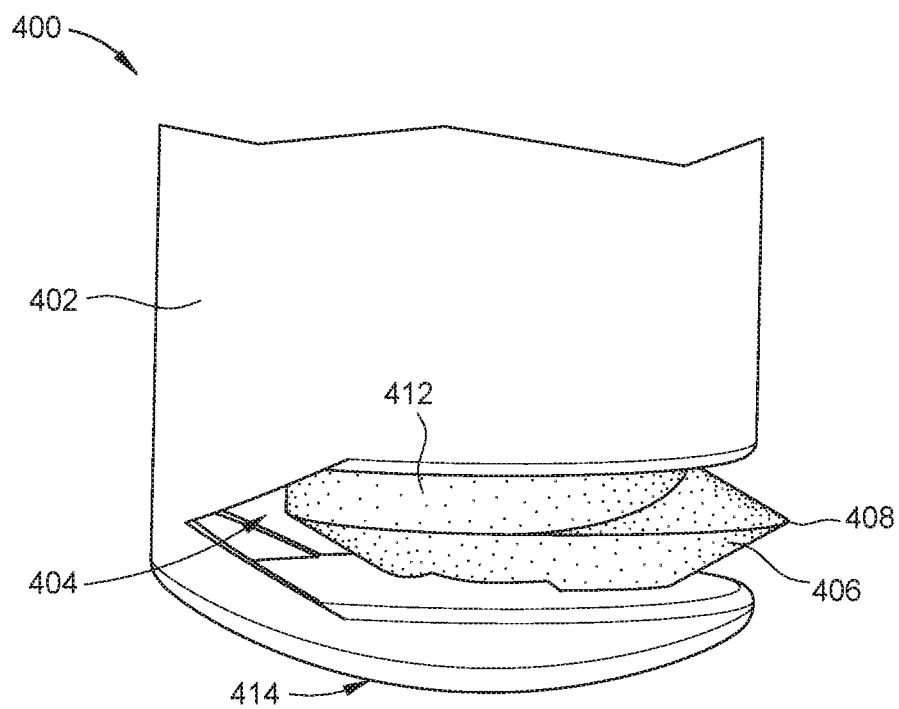
FIGS. 4A-4E illustrate another example rotational cutter including an off-center blade portion, in accordance with certain embodiments of the present disclosure.

FIGS. 4A-4D illustrate another example of a rotational cutter 400 including an off-center blade portion. FIG. 4A shows a side view of rotational cutter 400 having an outer shaft 402 and an inner shaft 412. Outer shaft 402 includes a bottom portion 414 at its distal end and an opening 404 in the side of outer shaft 202 near the distal end. Inner shaft 412 is disposed within and housed by outer shaft 402 and is configured to rotate within and with respect to outer shaft 402. For example, inner shaft 412 rotates around or with respect to a longitudinal axis of inner shaft 412. Inner shaft 412 includes a cylindrical portion that is housed within outer shaft 402 and blade portion 406 having a sharp tip 408 that is at least partially exposed by opening 404 in outer shaft 402. In certain embodiments, inner shaft 412 is coupled to driver (e.g., a motor or handle, as described above) that is configured to rotate inner shaft 412 within outer shaft 402. In certain embodiments, the driver may be configured to fully rotate inner shaft 412 around a longitudinal axis of outer shaft 402 at a certain speed. As shown, opening 404 of outer shaft 402 is configured such that blade portion 406 can fully rotate (e.g., 360 degrees or more) about the longitudinal axis of inner shaft 412. By rotating blade portion 406, sharp tip 408 is able to cut any connective tissue that it comes into contact with. In certain other embodiments, the driver may be configured to partially rotate inner shaft 412, and therefore blade portion 406, about the longitudinal axis of inner shaft 412 in an oscillating manner with a certain frequency, as described in relation to FIG. 5E.

Bottom portion 414 of outer shaft 402, which may also be referred to as the bottom portion 414 of rotational cutter 400, is curved as shown. Bottom portion 414 comprises curved or rounded edges. The curved bottom of bottom portion 414 as well as its rounded edges reduce the risk of any potential damage to the retina when a surgeon places bottom portion 414 on the surface of the retina.

Figure 4B:
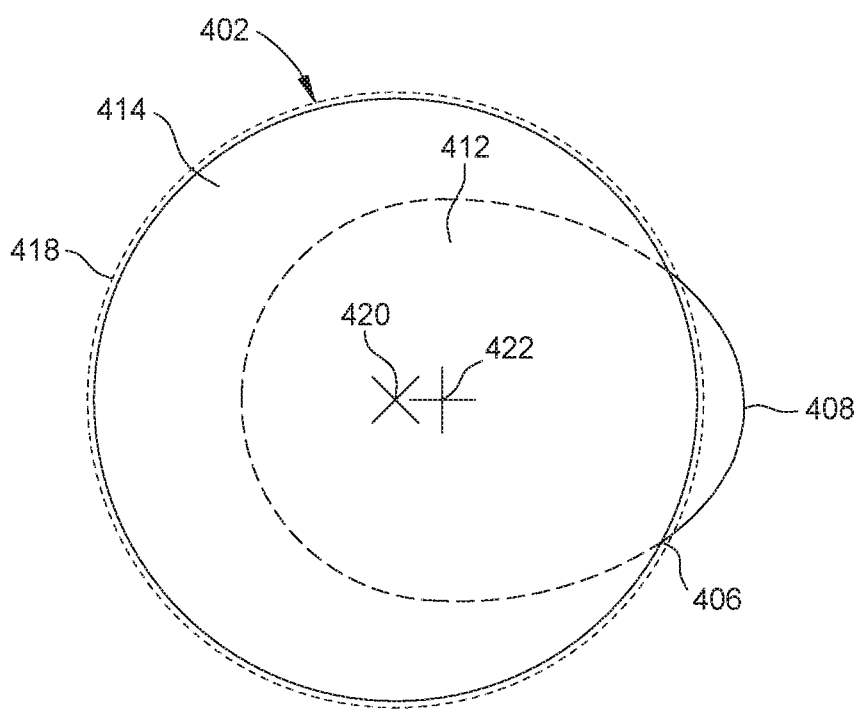

FIG. 4B illustrates a two-dimensional view of rotational cutter 400 of FIG. 4A from the bottom, looking along the longitudinal axis of the cutter. More specifically, FIG. 4B illustrates bottom portion 414 of outer shaft 402 as well as sharp tip 408 of blade portion 406, which extends outside a perimeter 418 of rotational cutter 400 for cutting purposes. FIG. 4B further illustrates the working principles of the off-center inner shaft 412. More specifically, bottom portion 414 has a center point 420 while inner shaft has a center point 422 that is not aligned with center point 420 (e.g., blade portion 406 is off-center with respect to bottom portion 414). Center port 422 may also be referred to as a pivot point 422, which corresponds to a point along a longitudinal axis of inner shaft 412 around which blade portion 406 rotates.

Figure 4C:
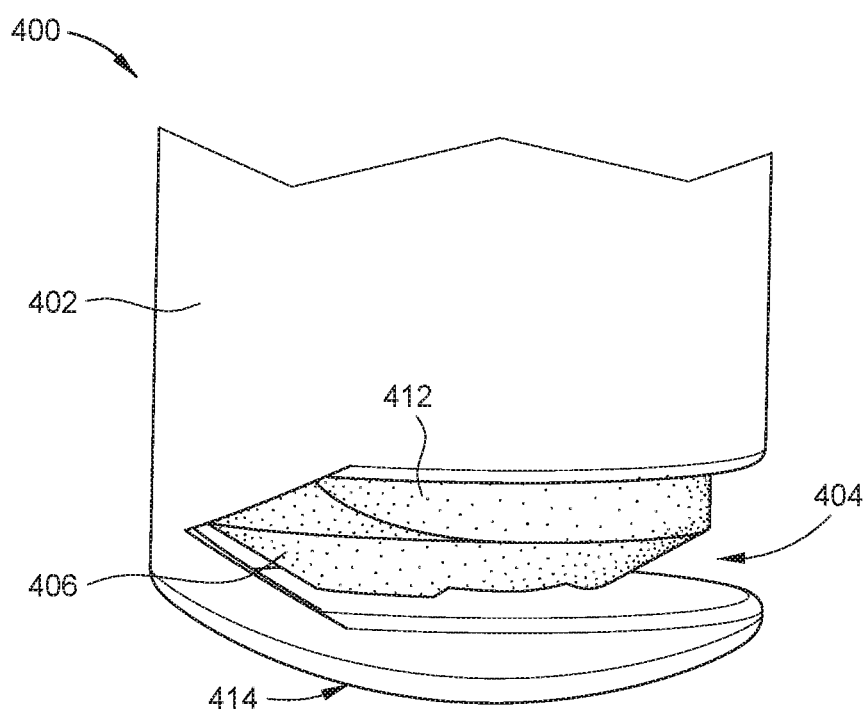

FIG. 4C illustrates a side view of rotational cutter 400, where blade portion 406 has rotated by 180 degrees in comparison to the state of blade portion 406 in FIG. 4A. As shown, in such a state, blade portion 406 is covered by outer shaft 402 such that tip 408 of blade portion 406 does not extend outside the perimeter of rotational cutter 400. As such, blade portion 406 may be referred to as being in a covered state.

Figure 4D:
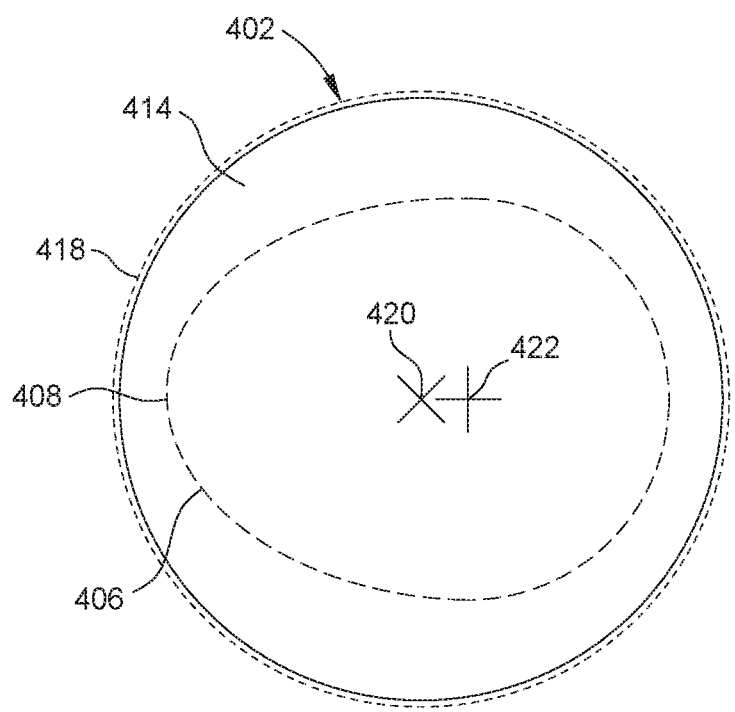

FIG. 4D illustrates rotational cutter 400 of FIG. 4C from the bottom. As shown, inner shaft 412 has rotated by 180 degrees around pivot point 422, as compared to its position in FIG. 4B. As further shown, in this position, sharp tip 408 of blade portion 406 does not extend outside perimeter 418 of rotational cutter 400. In certain embodiments, blade portion 406 may be placed in a covered state before a surgeon inserts rotational cutter 400 into the eye through the insertion cannula. However, once rotational cutter 400 is placed on the surface of the retina, the surgeon may activate rotational cutter 400, or the driver that is coupled to inner shaft 412, for membrane delamination, in which case the driver starts to rotate inner shaft 412, causing tip 408 to be uncovered and extend outside the perimeter 418 of outer shaft 402.

As discussed, in certain embodiments, when rotational cutter 400 is operational (i.e., when the driver that is coupled to inner shaft 412 is on), blade portion 406 fully rotates around pivot point 422. However, in other embodiments, the driver that is coupled to inner shaft 412 may be configured to only partially rotate inner shaft 412, and thereby blade portion 406, in an oscillating manner, as further shown in FIG. 4E.

Figure 4E:
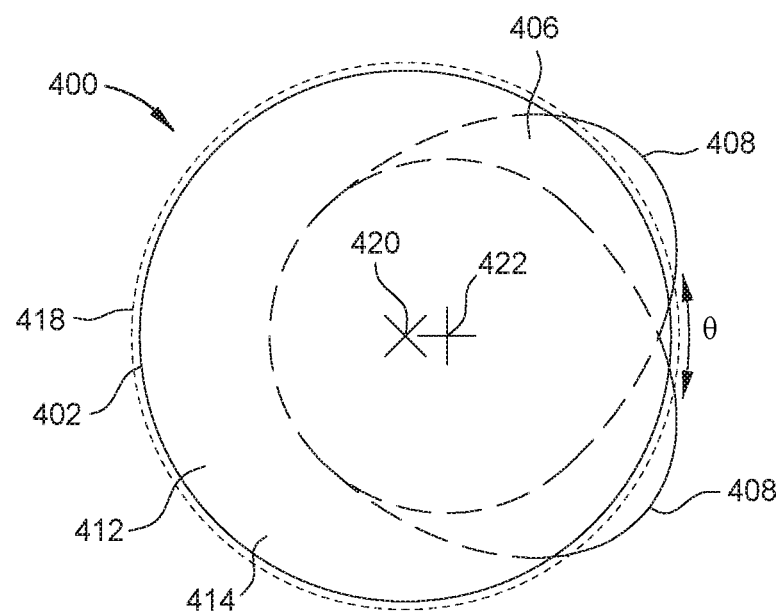

Similar to FIG. 4B, FIG. 4E illustrates a two-dimensional view of the oscillating motion of blade portion 406 from the bottom, looking along the longitudinal axis of the cutter. In FIG. 4E, inner shaft 412 rotates around pivot point 422, by a certain angle of rotation θ (e.g., less than 180 degrees), in an oscillating manner. In certain embodiments, the frequency or speed at which inner shaft 412 oscillates may be adjusted.

Figure 5:
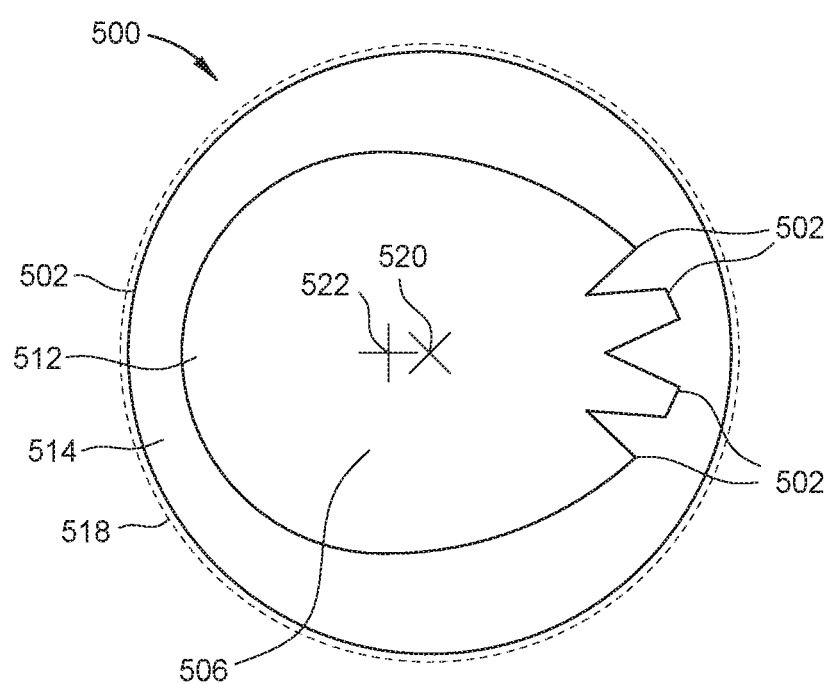
FIG. 5 illustrates an example blade portion with teeth, in accordance with certain embodiments of the present disclosure.

Note that the use of any combination of a blade (e.g., blade portion 406 with sharp tip 408) and teeth (e.g., the various upper and lower teeth shown in FIGS. 1A-3) within a rotational cutter is within the scope of this disclosure. For example, in FIGS. 1A and 1B, a blade portion, such as blade portion 406, may be used instead of one or both of upper teeth 107 and 109. Another example of a combination of some of the elements described above is shown in FIG. 5. FIG. 5 illustrates a two-dimensional view of rotational cutter 500, where blade portion 506 includes teeth 508. When rotational cutter 500 is operational, inner shaft 512 and blade portion 506 rotate (e.g., either fully or in an oscillating manner) around pivot point 522, which is not aligned with center point 520 of bottom portion 514. While rotating, teeth 508 extend outside perimeter 518 for cutting purposes.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A rotational cutter for delaminating a membrane from a retina of an eye, comprising:
    a first shaft;
    a second shaft comprising a blade portion, wherein the second shaft is coupled to a driver that is configured to at least partially rotate the second shaft relative to the first shaft, wherein rotating the second shaft rotates the blade portion for delaminating the membrane; and
    a bottom portion configured to interface with a surface of the retina, wherein the bottom portion comprises one or more curved edges;
    wherein:
        the blade portion comprises upper teeth; and
        the first shaft comprises:
            an exposed portion configured to interface with the surface of the retina, the exposed portion having a curved back surface extending continuously from a proximal end of the exposed portion to the bottom portion; and
            a second blade portion including the bottom portion, wherein the second blade portion comprises lower teeth;
    wherein the lower teeth comprise a plurality of teeth between a left-most outer tooth and an opposing right-most outer tooth, wherein the left-most outer tooth has a greater height on a right side of the left-most outer tooth than a left side of the left-most outer tooth and the right-most outer tooth has a greater height on a left side of the rightmost outer tooth than a right side of the right-most outer tooth;
    wherein the left-most outer tooth and the right-most outer tooth have a curved bottom edge extending between their respective left and right sides.

2. The rotational cutter of claim 1, wherein the first shaft is an inner shaft and wherein the second shaft is an outer shaft that at least partially houses the first shaft.

3. The rotational cutter of claim 1, wherein the driver being configured to at least partially rotate the second shaft relative to the first shaft comprises:
    the driver being configured to rotate the second shaft in a first direction with respect to the first shaft causing the blade portion to slide in the first direction with respect to the second blade portion;
    the driver being configured to rotate the second shaft in a second direction, with respect to the first shaft causing the blade portion to slide in the second direction with respect to the second blade portion.

4. The rotational cutter of claim 3, wherein the driver being configured to at least partially rotate the second shaft relative to the first shaft comprises the driver being configured to at least partially rotate the second shaft relative to the first shaft in an oscillating manner.

5. The rotational cutter of claim 4, wherein:
    rotation of the second shaft in the first direction ends when a first outer tooth of the upper teeth is aligned with a first outer tooth of the lower teeth; and
    rotation of the second shaft in the second direction ends when a second outer tooth of the upper teeth is aligned with a second outer tooth of the lower teeth.

* * * * *